(12) United States Patent
Hiraoka (10) Patent No.: US 11,805,987 B2
(45) Date of Patent: Nov. 7, 2023

(54) ENDOSCOPE HAVING DISTAL-END RIGID PORTION WITH ROTATABLE RAISING BASE

(71) Applicant: OLYMPUS CORPORATION, Tokyo (JP)

(72) Inventor: Jin Hiraoka, Sagamihara (JP)

(73) Assignee: OLYMPUS CORPORATION, Tokyo (JP)

(*) Notice: Subject to any disclaimer, the term of this patent is extended or adjusted under 35 U.S.C. 154(b) by 618 days.

(21) Appl. No.: 16/983,287

(22) Filed: Aug. 3, 2020

(65) Prior Publication Data

US 2020/0359880 A1 Nov. 19, 2020

Related U.S. Application Data

(63) Continuation of application No. PCT/JP2018/044576, filed on Dec. 4, 2018.

(30) Foreign Application Priority Data

Feb. 5, 2018 (JP) .................................. 2018-018463

(51) Int. Cl.
*A61B 1/018* (2006.01)
*A61B 1/00* (2006.01)
(Continued)

(52) U.S. Cl.
CPC .......... *A61B 1/018* (2013.01); *A61B 1/00006* (2013.01); *A61B 1/00087* (2013.01);
(Continued)

(58) Field of Classification Search
CPC . A61B 1/018; A61B 1/00006; A61B 1/00087; A61B 1/00137; A61B 1/051;
(Continued)

(56) References Cited

U.S. PATENT DOCUMENTS

2012/0078041 A1* 3/2012 Kitano ............... A61B 1/00098
600/107
2017/0112362 A1* 4/2017 Morimoto .......... A61B 1/00098
(Continued)

FOREIGN PATENT DOCUMENTS

JP 2016-131578 A 7/2016
JP 2017-079877 A 5/2017
(Continued)

OTHER PUBLICATIONS

International Search Report dated Feb. 5, 2019 issued in PCT/JP2018/044576.

*Primary Examiner* — John P Leubecker
*Assistant Examiner* — Li-Ting Song
(74) *Attorney, Agent, or Firm* — Scully, Scott, Murphy & Presser, P.C.

(57) ABSTRACT

An endoscope includes: a distal-end rigid portion including an opening through which an instrument protrudes; a raising base disposed in the opening and configured to change a direction in which the instrument protrudes; a rotary shaft fixed to the raising base so as to rotate together with the raising base; an arm fixed to the rotary shaft so as to rotate the rotary shaft; a housing formed separately from the distal-end rigid portion, the housing including: a first bearing including a first shaft hole to rotatably support the rotary shaft; and a second bearing integrally formed with the first bearing and including a second shaft hole that is coaxially arranged with the first shaft hole so as to rotatably support the rotary shaft; and a seal member disposed between an outer circumference of the rotary shaft and an inner circumference of the first shaft hole to keep watertightness therebetween.

20 Claims, 13 Drawing Sheets (51) Int. Cl.
*A61B 1/005* (2006.01)
*A61B 1/06* (2006.01)

(52) U.S. Cl.
CPC ........ *A61B 1/00137* (2013.01); *A61B 1/0051* (2013.01); *A61B 1/0661* (2013.01)

(58) Field of Classification Search
CPC .............. A61B 1/00101; A61B 1/0011; A61B 1/00098
USPC ........................................................ 600/107
See application file for complete search history.

(56) References Cited

U.S. PATENT DOCUMENTS

| | | | |
|---|---|---|---|
| 2017/0112363 A1 | 4/2017 | Morimoto | |
| 2018/0092512 A1* | 4/2018 | Hiraoka | A61B 1/00 |
| 2018/0185045 A1* | 7/2018 | Ohki | A61B 1/009 |
| 2019/0038114 A1 | 2/2019 | Hiraoka | |
| 2019/0117045 A1* | 4/2019 | Hosogoe | A61B 1/00 |
| 2019/0239739 A1* | 8/2019 | Hiraoka | A61B 1/00098 |
| 2019/0307317 A1* | 10/2019 | Matsubara | A61B 1/018 |
| 2020/0352423 A1* | 11/2020 | Hayakawa | A61B 1/00087 |
| 2020/0397233 A1* | 12/2020 | Hosogoe | G02B 23/24 |
| 2021/0169308 A1* | 6/2021 | Fukuzawa | A61B 1/0623 |
| 2021/0169312 A1* | 6/2021 | Morimoto | A61B 1/0011 |
| 2022/0400934 A1* | 12/2022 | Morimoto | A61B 1/00098 |
| 2023/0000318 A1* | 1/2023 | Yamaya | A61B 1/00101 |

FOREIGN PATENT DOCUMENTS

| | | |
|---|---|---|
| WO | WO 2017/179293 A1 | 10/2017 |
| WO | WO 2018/012486 A1 | 1/2018 |

* cited by examiner

ENDOSCOPE HAVING DISTAL-END RIGID PORTION WITH ROTATABLE RAISING BASE

This application is a continuation of PCT International Application No. PCT/JP2018/044576 filed on Dec. 4, 2018, which designates the United States, incorporated herein by reference, and which claims the benefit of priority from Japanese Patent Application No. 2018-018463, filed on Feb. 5, 2018, incorporated herein by reference.

BACKGROUND

The present disclosure relates to an endoscope.

There are known endoscopes in which an instrument such as forceps may protrude from the distal end of an insertion unit inserted into a subject (see, for example, Japanese Laid-open Patent Publication No. 2016-131578). In this endoscope, an operation wire extending in the insertion unit is moved in accordance with the operation on an operating unit provided on the proximal end side of the insertion unit so that a rotary shaft rotates to raise an elevator. In the known endoscope, the rotary shaft is supported by a shaft hole of a housing disposed between the connection position of the wire and the elevator.

SUMMARY

According to one aspect of the present disclosure, there is provided an endoscope through which an instrument is insertable including: a distal-end rigid portion disposed at a distal end of the endoscope and including an opening through which the instrument protrudes; a raising base disposed in the opening and configured to be in contact with the instrument and change a direction in which the instrument protrudes; a rotary shaft having one end thereof fixed to the raising base so as to rotate together with the raising base; an arm fixed to the rotary shaft so as to rotate the rotary shaft in accordance with an operation on an operating unit; a housing formed separately from the distal-end rigid portion, the housing including: a first bearing located closer to the raising base than the arm in an axial direction of the rotary shaft and including a first shaft hole to rotatably support the rotary shaft; and a second bearing integrally formed with the first bearing and located on a side opposite to the first bearing with respect to the arm unit in the axial direction, the second bearing including a second shaft hole that is coaxially arranged with the first shaft hole so as to rotatably support the rotary shaft; and a seal member disposed between an outer circumference of the rotary shaft and an inner circumference of the first shaft hole to keep watertightness between the rotary shaft and the first shaft hole.

The above and other features, advantages and technical and industrial significance of this disclosure will be better understood by reading the following detailed description of presently preferred embodiments of the disclosure, when considered in connection with the accompanying drawings.

DETAILED DESCRIPTION

An embodiment of an endoscope is described below with reference to the drawings. The present disclosure is not limited to the embodiment. The present disclosure is applicable to typical endoscopes including a raising base.

In the description of the drawings, the identical or corresponding elements are denoted by the same reference numeral as appropriate. It should be noted that the drawings are schematic and the relationship between the elements in dimension, the ratio of the elements, and the like, are sometimes different from the reality. In the drawings, some of the elements may be different in the dimensional relationship or the ratio.

Figure 1:
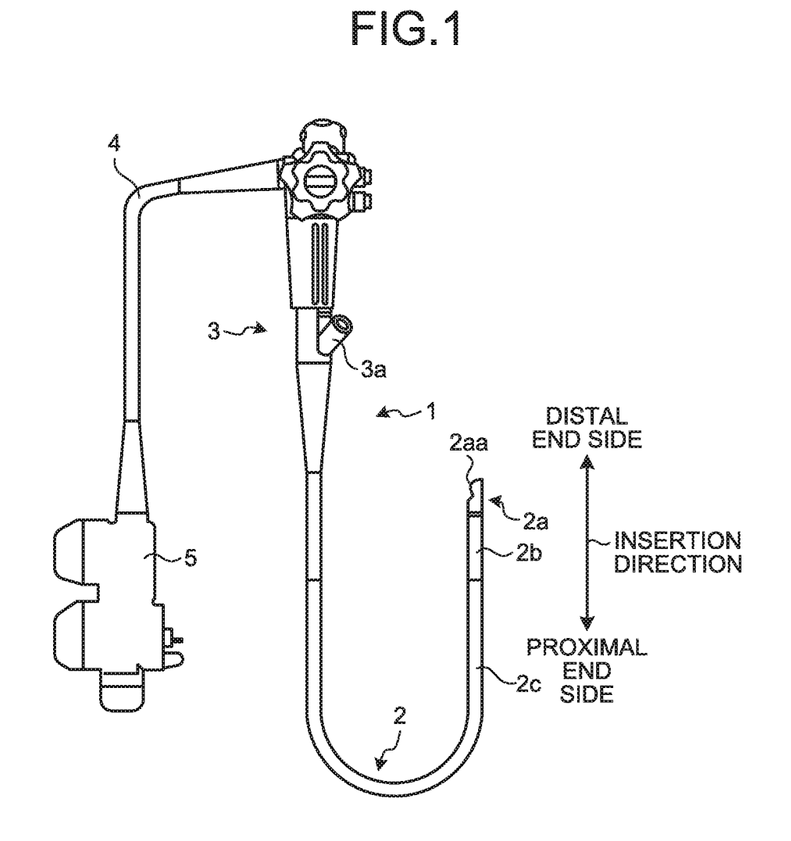
FIG. 1 is a schematic view illustrating a configuration of an endoscope according to an embodiment.

FIG. 1 is a schematic view illustrating a configuration of an endoscope 1 according to an embodiment. The endoscope 1 includes: an insertion unit 2 having an imaging unit installed at its distal end and inserted into the inside of the subject; an operating unit 3 continuously coupled to the proximal end side of the insertion unit 2; a universal cord 4 extending from the side of the operating unit 3; and a connector unit 5 continuously coupled to the universal cord 4 and coupled to an observation device that controls the endoscope 1, a light source device that supplies illumination light to the endoscope 1, and the like. In this description, as illustrated in FIG. 1, the direction that is the longitudinal direction of the endoscope 1 and that is the insertion direction of the insertion unit 2 is referred to as an "insertion direction", the distal end side (the upper side in FIG. 1) in the insertion direction as the "distal end side", and the proximal end side (the lower side in FIG. 1) as the "proximal end side".

The insertion unit 2 includes, sequentially from the distal end side, a distal end portion 2a, a bendable portion 2b that is configured to bend in accordance with the operation of the operating unit 3, and a flexible tube portion 2c having flexibility. The proximal end of the flexible tube portion 2c is continuously coupled to the distal end side of the operating unit 3. An ultrasound transducer 2aa is disposed at the distal end of the distal end portion 2a. The endoscope 1 may be an endoscope including no ultrasound transducer.

The operating unit 3 includes a forceps insertion port 3a through which an instrument such as a forceps needle is inserted into the subject. A forceps insertion channel is provided inside the insertion unit 2, and therefore the forceps insertion port 3a serves as an insertion port of the forceps insertion channel. That is, the endoscope 1 is an endoscope through which an instrument is insertable. The operating unit 3 receives the operation for rotating a rotary shaft described later.

Figure 2:
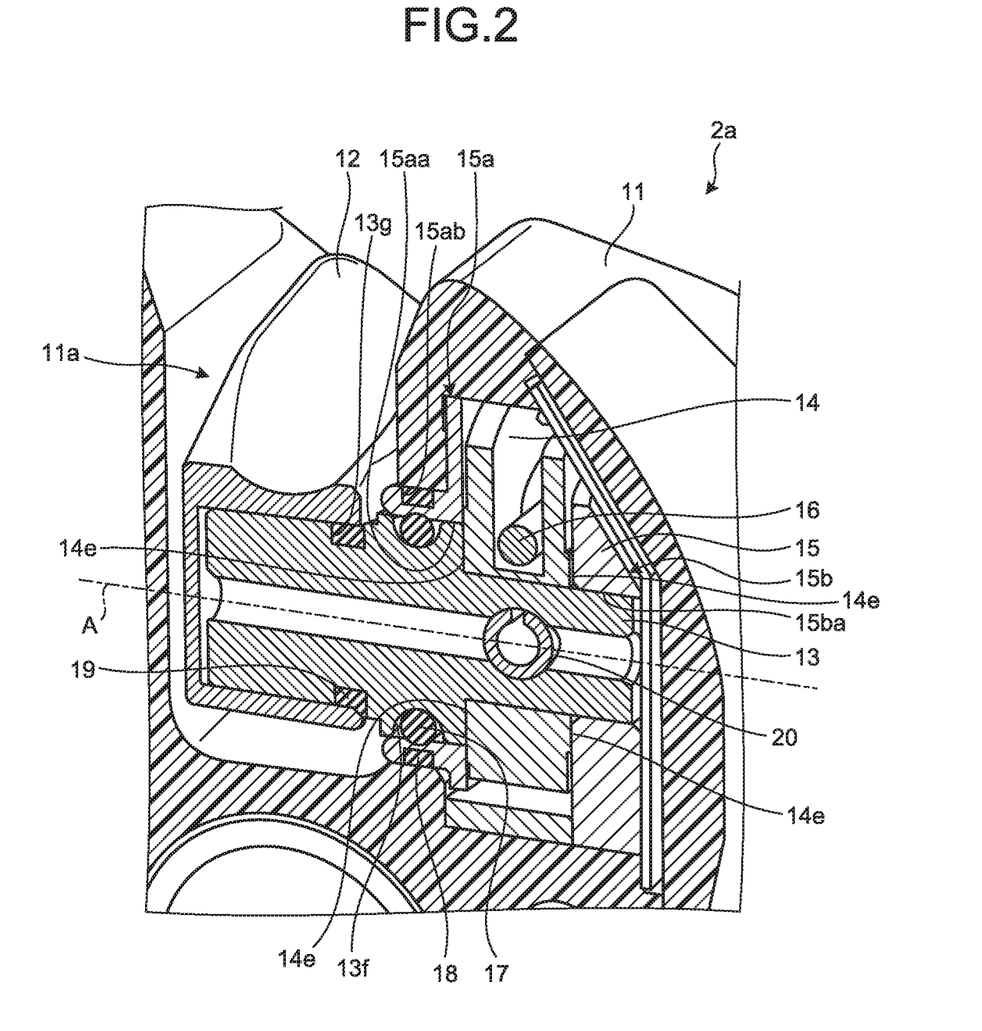
FIG. 2 is a schematic partial cross-sectional view of a distal end portion of the endoscope illustrated in FIG. 1.

FIG. 2 is a schematic partial cross-sectional view of the distal end portion 2a of the endoscope 1 illustrated in FIG. 1. FIG. 2 illustrates the cross-section perpendicular to the insertion direction. As illustrated in FIG. 2, the distal end portion 2a of the endoscope 1 includes: a distal-end rigid portion 11 disposed at the distal end of the endoscope 1 and having an opening 11a formed therein; a forceps elevator (raising base) 12 disposed in the opening 11a to be in contact with the forceps and change the protruding direction of the forceps; a rotary shaft 13 having one end thereof fixed to the forceps elevator 12 so as to rotate together with the forceps elevator 12 around an axis A; and an arm unit 14 fixed to the rotary shaft 13 so as to rotate the rotary shaft 13 in accordance with the operation on the operating unit 3; a housing 15 rotatably supporting the rotary shaft 13; a rotary shaft seal 17 serving as a sealing member that keeps the watertightness between the rotary shaft 13 and the housing 15; a housing seal 18 keeping the watertightness between the distal-end rigid portion 11 and the housing 15; a forceps elevator seal (raising base seal) 19 keeping the watertightness between the forceps elevator 12 and the rotary shaft 13; and a spring pin 20 fixing the rotary shaft 13 to the arm unit 14.

The distal-end rigid portion 11 is made of, for example, a resin.

Figure 3:
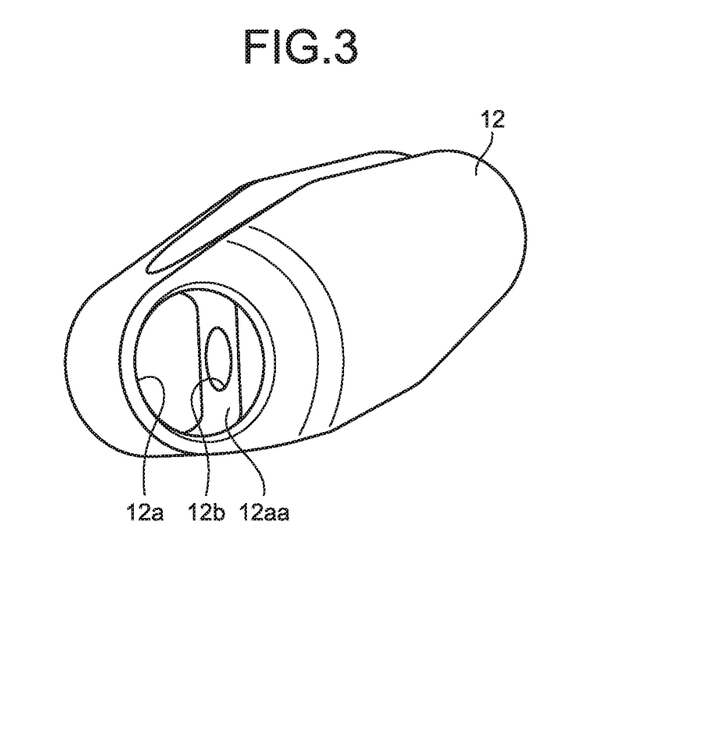
FIG. 3 is a side view of a forceps elevator illustrated in FIG. 2.

FIG. 3 is a side view of the forceps elevator 12 illustrated in FIG. 2. As illustrated in FIG. 3, the side surface of the forceps elevator 12 includes a shaft hole 12a to be engaged with the rotary shaft 13. The shaft hole 12a includes a planar portion 12aa extending in the direction perpendicular to the axial direction (the axis A) of the rotary shaft 13. The forceps elevator 12 includes a screw hole 12b communicating with the shaft hole 12a. With reference back to FIG. 2, the outer circumference of the rotary shaft 13 includes an engagement groove 13f to be engaged with the rotary shaft seal 17. The forceps elevator 12 is made of a rigid material such as a metal, an alloy, or a ceramic.

Figure 4:
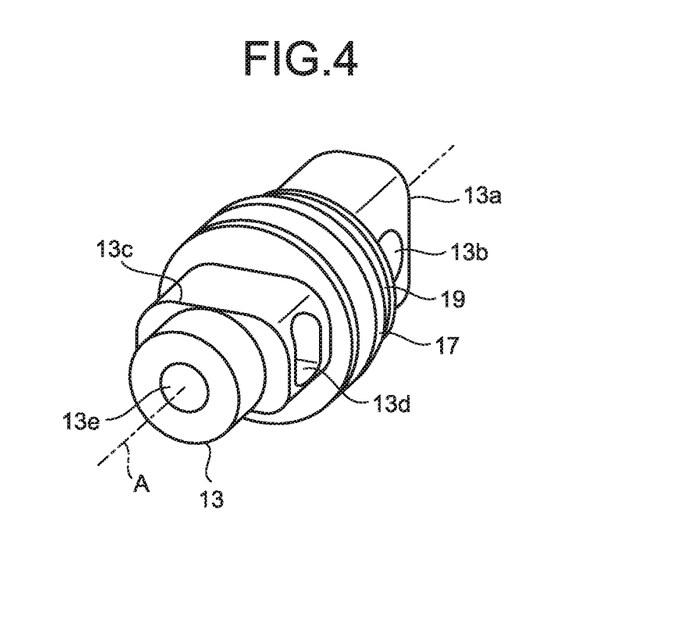
FIG. 4 is a perspective view of a rotary shaft illustrated in FIG. 2.

FIG. 4 is a perspective view of the rotary shaft 13 illustrated in FIG. 2. As illustrated in FIG. 4, the rotary shaft 13 includes a planar portion 13a extending in a direction perpendicular to the axial direction (the axis A) of the rotary shaft 13 and opposed to the planar portion 12aa of the shaft hole 12a. The planar portion 13a includes a groove 13b in which the distal end of the screw engaged with the screw hole 12b is positioned. The outer circumference of the rotary shaft 13 on the side opposite to the forceps elevator 12 includes a planar portion 13c extending in the direction perpendicular to the axial direction (the axis A). A pin hole 13d into which the spring pin 20 is inserted is formed inside the planar portion 13c. A through-hole 13e is formed inside the rotary shaft 13 so as to check the watertightness between the forceps elevator 12 and the rotary shaft 13. Specifically, the watertightness between the forceps elevator 12 and the rotary shaft 13 may be checked depending on the escape of gas when the gas is introduced through the through-hole 13e from the side opposite to the forceps elevator 12 while the contact part between the forceps elevator 12 and the forceps elevator seal 19 is immersed in liquid. The rotary shaft 13 is made of, for example, a metal or an alloy. It is preferable that coating is applied to the surface of the rotary shaft 13 so as to improve the sliding performance. Specifically, coating such as DLC (Diamond-Like Carbon), fluorine, or plating is applied to the surface of the rotary shaft 13. In the endoscope 1, the rotary shaft 13 slides relative to the rotary shaft seal 17; however, when the housing 15 slides relative to the rotary shaft seal 17, it is preferable to apply the above-described coating to the surface of the housing 15.

Figure 5:
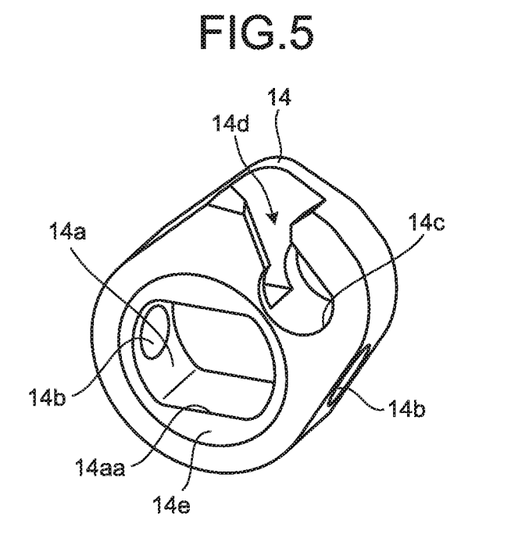
FIG. 5 is a perspective view of an arm unit illustrated in FIG. 2.

FIG. 5 is a perspective view of the arm unit 14 illustrated in FIG. 2. As illustrated in FIG. 5, the arm unit 14 includes a through-hole 14a through which the rotary shaft 13 is inserted. The through-hole 14a includes a planar portion 14aa extending in the direction perpendicular to the axial direction (the axis A) and opposed to the planar portion 13c of the rotary shaft 13. In the assembled endoscope 1, the through-hole 14a is engaged with the rotary shaft 13 in a state where the planar portion 14aa of the through-hole 14a is opposed to the planar portion 13c of the rotary shaft 13. The arm unit 14 includes a pin hole 14b through which the spring pin 20 is inserted. The through-hole 14a is engaged with the rotary shaft 13 and the spring pin 20 is inserted into the pin hole 13d and the pin hole 14b so that the rotary shaft 13 and the arm unit 14 may rotate together. The arm unit 14 includes a wire engagement portion 14c that engages with a cylindrical wire distal end portion 16a formed at the distal end of a forceps operation wire 16. Furthermore, the arm unit 14 includes a slit 14d communicating with the wire engagement portion 14c so as to insert the wire distal end portion 16a into the wire engagement portion 14c. The slit 14d is formed at such a position that the wire distal end portion 16a is insertable from above in FIG. 5 in a state where the forceps operation wire 16 is located closest to the proximal end side (a state where the forceps elevator 12 is elevated). As a result, as the part receiving a force applied to the arm unit 14 via the forceps operation wire 16 has a large area, it is possible to prevent the deformation of the arm unit 14. The outer peripheries of the through-holes 14a on both side surfaces of the arm unit 14 include stepped portions 14e (see FIG. 2 and FIG. 5). The formation of the stepped portions 14e prevents the displacement of the arm unit 14 in the axial direction (the axis A) with respect to the housing 15. As a result, the forceps elevator 12 is prevented from moving in the axial direction (the axis A) and the forceps elevator 12 is allowed to be elevated right above with accuracy, whereby it is possible to prevent the forceps elevator 12 from being in contact with the wall surface of the distal-end rigid portion 11, maintain a certain clearance between the wall surface of the distal-end rigid portion 11 and the forceps elevator 12, and ensure the cleanability. Moreover, the formation of the stepped portions 14e may reduce the contact area between the arm unit 14 and the housing 15 and decrease the frictional resistance between the arm unit 14 and the housing 15. The arm unit 14 is made of, for example, a metal or an alloy.

Figure 6:
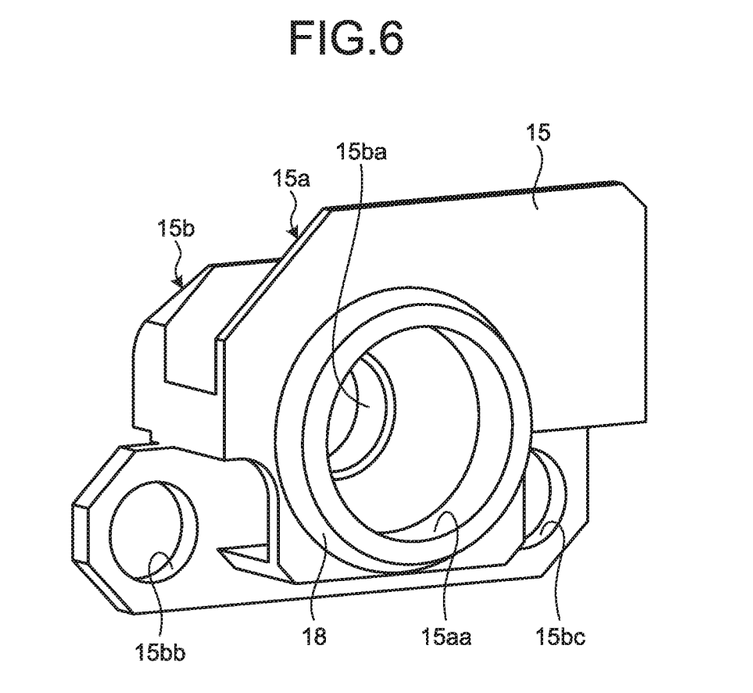
FIG. 6 is a perspective view of a housing illustrated in FIG. 2.

FIG. 6 is a perspective view of the housing 15 illustrated in FIG. 2. As illustrated in FIG. 6, the housing 15 includes: a first bearing portion 15a that is located closer to the forceps elevator 12 than the arm unit 14 in the axial direction (the axis A) of the rotary shaft 13; and a second bearing portion 15b that is located on the side opposite to the first bearing portion 15a with respect to the arm unit 14 in the axial direction (the axis A). The housing 15 is made of, for example, a metal or an alloy and has the first bearing portion 15a and the second bearing portion 15b integrally formed.

The first bearing portion 15a includes a first shaft hole 15aa that rotatably supports the rotary shaft 13. The second bearing portion 15b includes a second shaft hole 15ba that is coaxially arranged with the first shaft hole 15aa and rotatably supports the rotary shaft 13. The second bearing portion 15b includes a screw hole 15bb and a screw hole 15bc used to fix the housing 15 to the distal-end rigid portion 11.

With reference back to FIG. 2, the forceps operation wire 16 extends toward the proximal end side and moves in the insertion direction in accordance with the operation on the operating unit 3 so as to rotate the forceps elevator 12 via the arm unit 14 and the rotary shaft 13.

The rotary shaft seal 17 is disposed between the engagement groove 13f positioned on the outer circumference of the rotary shaft 13 and the inner circumference of the first shaft hole 15aa of the first bearing portion 15a. The rotary shaft seal 17 is made of a material having elasticity, such as rubber or silicone.

The housing seal 18 is disposed between a groove 15ab formed in the first bearing portion 15a and the distal-end rigid portion 11. The housing seal 18 is made of a material having elasticity, such as rubber or silicone.

The forceps elevator seal 19 is disposed between a groove 13g formed on the outer circumference of the rotary shaft 13 and the forceps elevator 12. The forceps elevator seal 19 is made of a material having elasticity, such as rubber or silicone.

Figure 7:
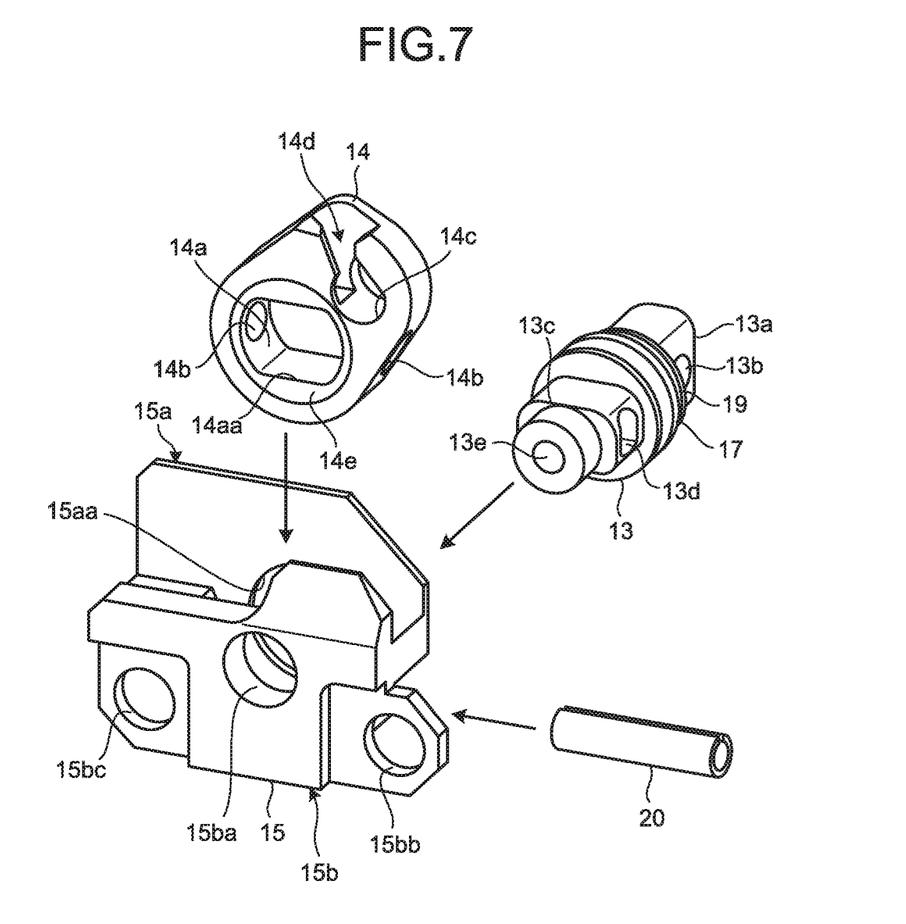
FIG. 7 is a diagram illustrating a method for assembling the endoscope.
Figure 8:
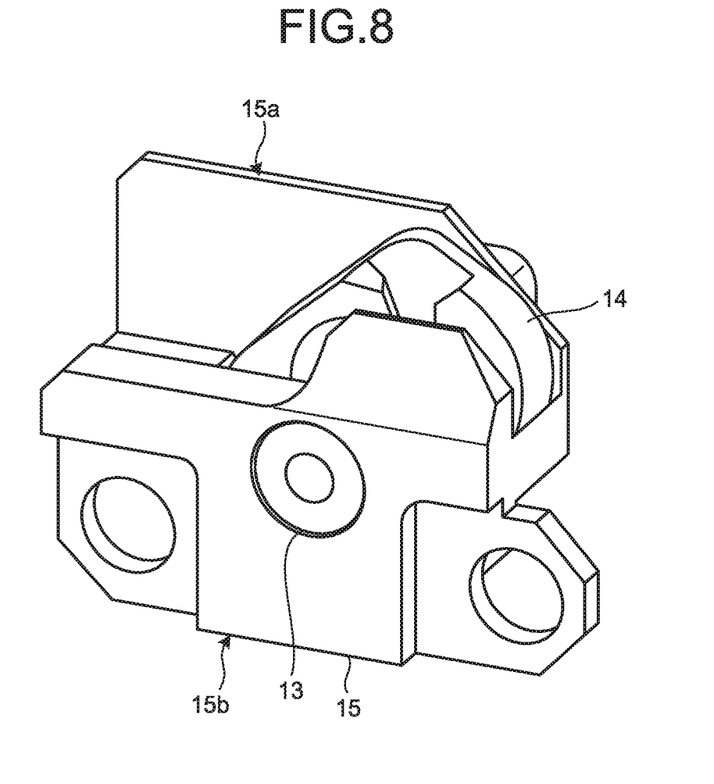
FIG. 8 is a diagram illustrating the method for assembling the endoscope.

Next, the method for assembling the endoscope 1 is described. FIGS. 7 to 13 are diagrams illustrating the method for assembling the endoscope 1. First, as illustrated in FIG. 7, the arm unit 14 is disposed between the first bearing portion 15a and the second bearing portion 15b of the housing 15. Then, the rotary shaft 13 is engaged with the through-hole 14a of the arm unit 14 and the second shaft hole 15ba of the second bearing portion 15b via the first shaft hole 15aa of the first bearing portion 15a such that the planar portion 14aa of the arm unit 14 is opposed to the planar portion 13c of the rotary shaft 13. Then, the spring pin 20 is inserted into the pin hole 14b of the arm unit 14 and the pin hole 13d of the rotary shaft 13. Accordingly, a raising base unit illustrated in FIG. 8 is assembled. In this state, as the rotation axis of the forceps elevator 12, the rotation axis of the arm unit 14, and the axis centers of the first shaft hole 15aa and the second shaft hole 15ba are in the identical straight line, there is no need for alignment.

Figure 9:
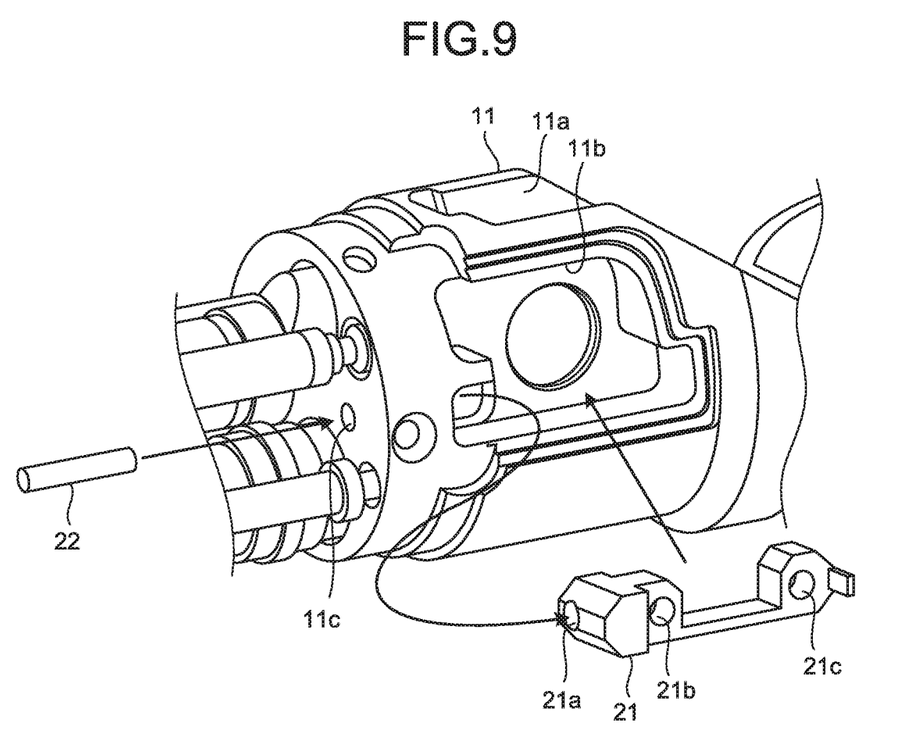
FIG. 9 is a diagram illustrating the method for assembling the endoscope.

Subsequently, as illustrated in FIG. 9, a base 21 is fitted into an opening 11b of the distal-end rigid portion 11. The base 21 is made of a metal or an alloy and is a base for attaching the raising base unit illustrated in FIG. 8. A pin 22 is inserted into a pin hole 21a of the base 21 through a pin hole 11c of the distal-end rigid portion 11. The base 21 is attached to the distal-end rigid portion 11 with an adhesive, or the like. The base 21 includes a screw hole 21b and a screw hole 21c.

Figure 10:
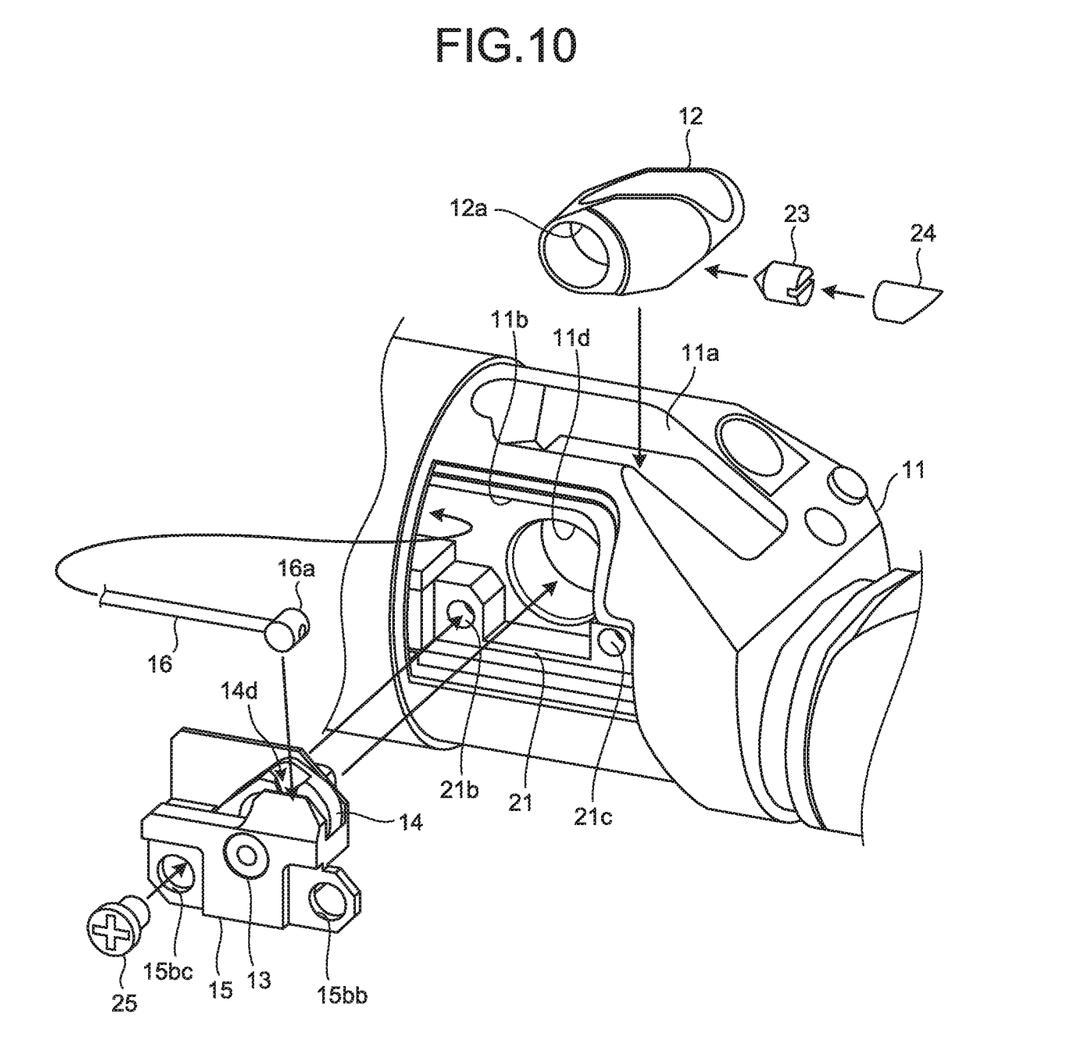
FIG. 10 is a diagram illustrating the method for assembling the endoscope.

Then, as illustrated in FIG. 10, in a state where the forceps elevator 12 is disposed in the opening 11a of the distal-end rigid portion 11, the raising base unit illustrated in FIG. 8 is inserted into the opening 11b of the distal-end rigid portion 11. Here, the outer circumference of the first shaft hole 15aa of the first bearing portion 15a is engaged with a through-hole 11d of the distal-end rigid portion 11. The rotary shaft 13 is inserted into the shaft hole 12a of the forceps elevator 12. A screw 25 is fitted into the screw hole 21b of the base 21 via the screw hole 15bc of the second bearing portion 15b. The wire distal end portion 16a of the forceps operation wire 16 is assembled with the wire engagement portion 14c of the arm unit 14 via the slit 14d.

Figure 11:
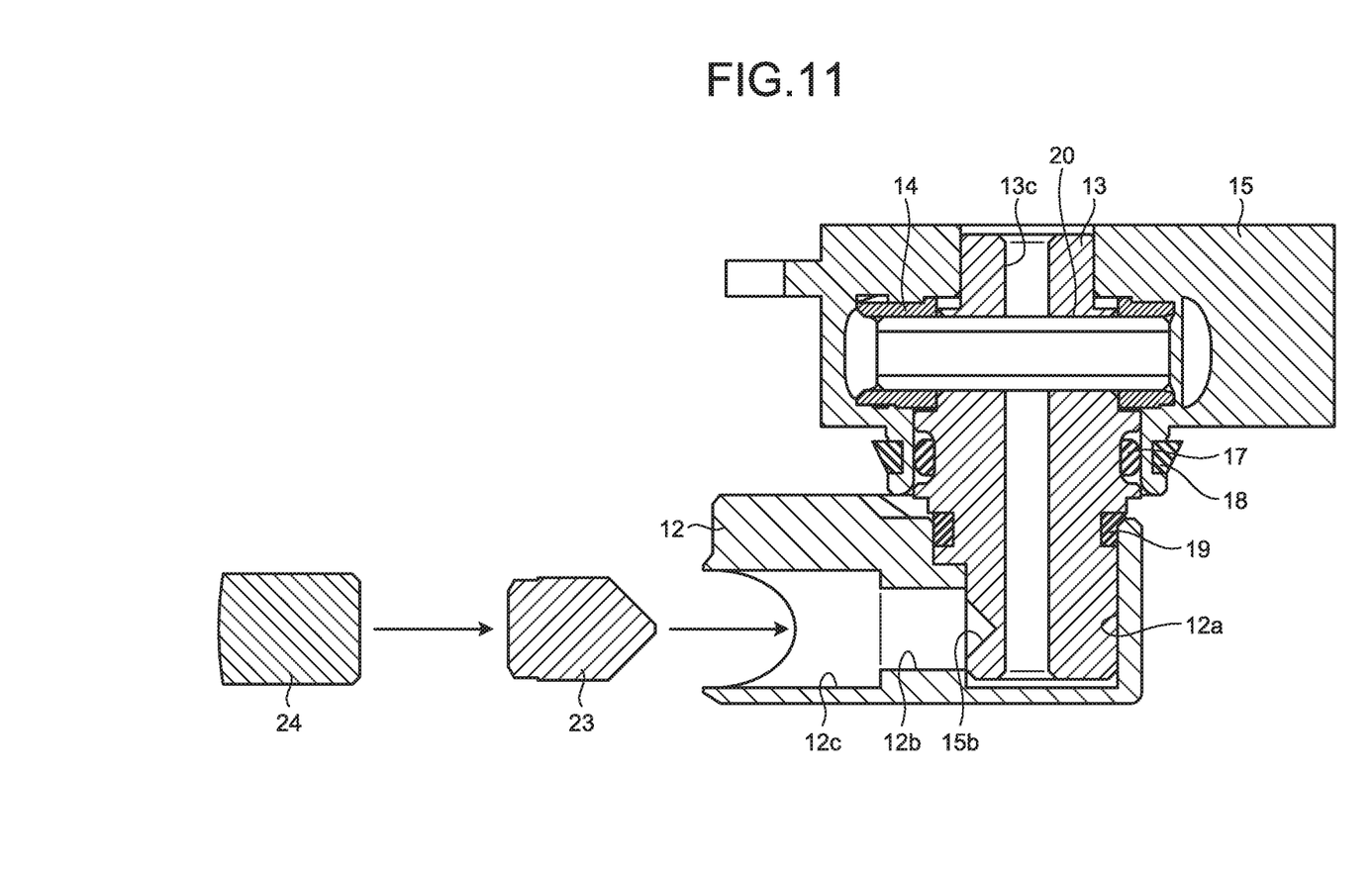
FIG. 11 is a diagram illustrating the method for assembling the endoscope.

FIG. 11 is a cross-sectional view along the axis A that is the rotation axis of the rotary shaft 13. As illustrated in FIG. 11, a screw 23 is fitted into the screw hole 12b of the forceps elevator 12 in a state where the rotary shaft 13 is inserted into the through-hole 11d of the distal-end rigid portion 11. Accordingly, the forceps elevator 12 and the rotary shaft 13 are fixed to each other. A groove 12c of the forceps elevator 12 is sealed by a screw concealing member 24 to which an adhesive is applied.

Figure 12:
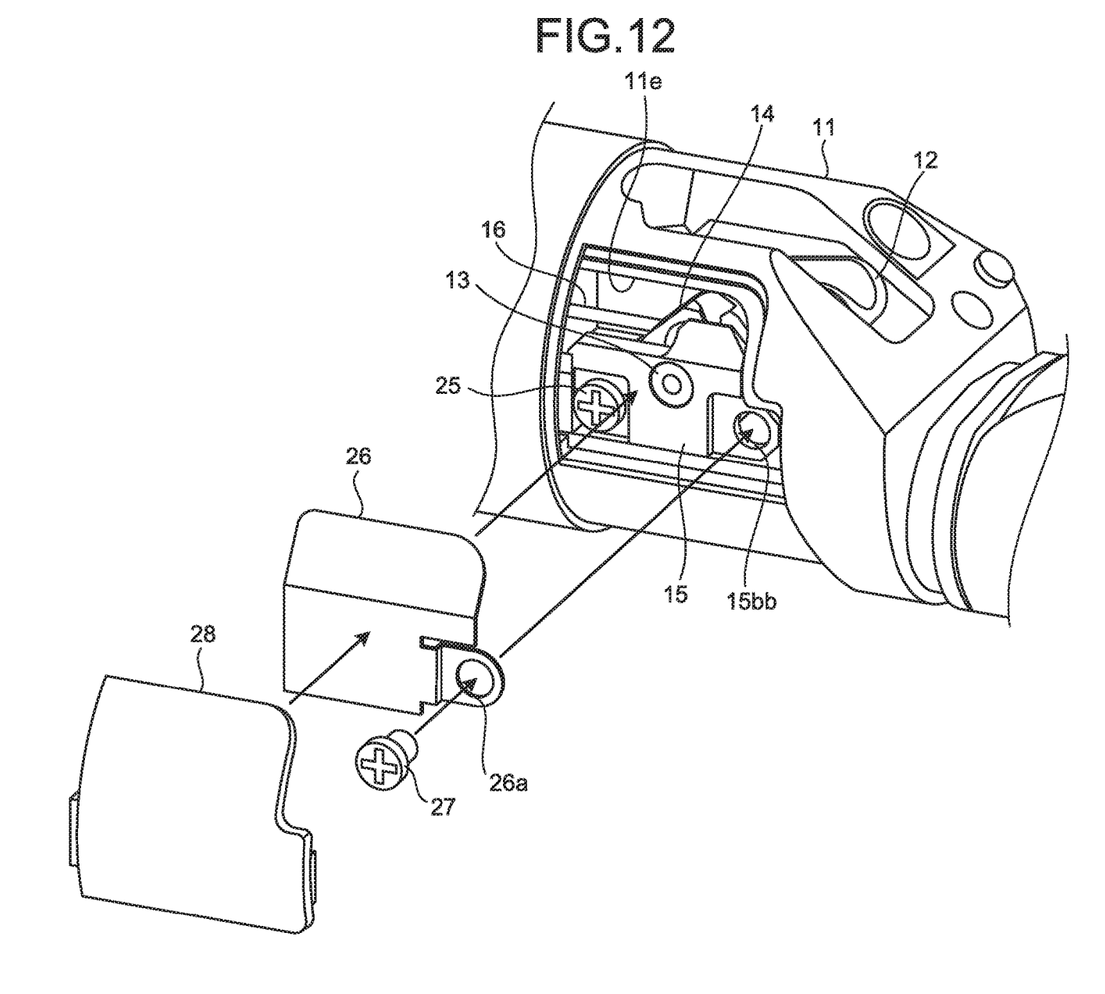
FIG. 12 is a diagram illustrating the method for assembling the endoscope.
Figure 13:
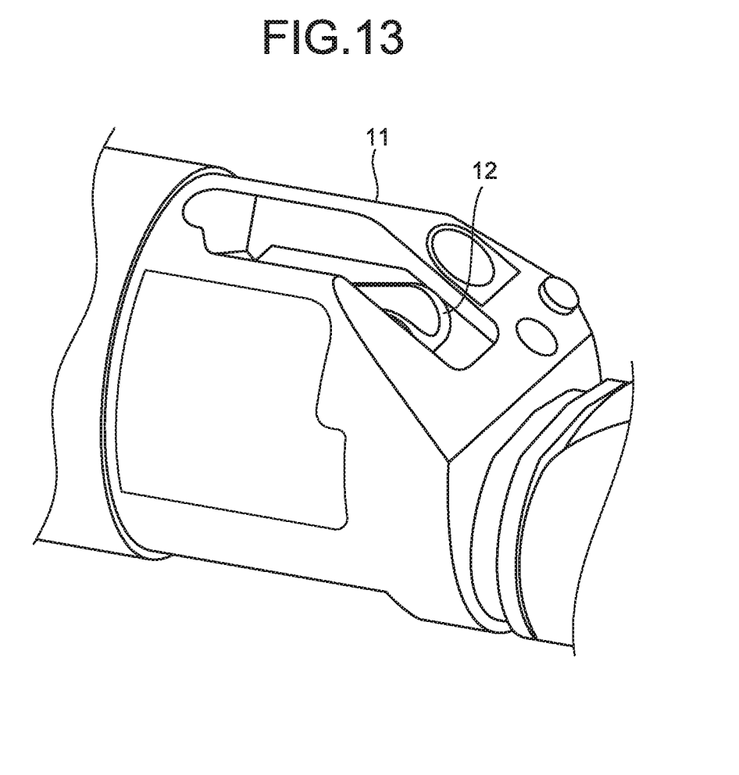
FIG. 13 is a diagram illustrating the method for assembling the endoscope.

Finally, as illustrated in FIG. 12, a cover 26 is bonded with an adhesive, or the like, so as to cover a stepped portion 11e of the distal-end rigid portion 11, and a screw 27 is fitted into the screw hole 21c via a hole 26a and the screw hole 15bb. Accordingly, the watertightness of the space closer to the cover 26 with respect to the rotary shaft seal 17 is maintained. Furthermore, a lid 28 is bonded over the cover 26 with an adhesive. As a result, the distal end portion of the endoscope 1 illustrated in FIG. 13 is assembled.

As described above, according to the embodiment, as the two sides of the rotary shaft 13 are supported by the first shaft hole 15aa and the second shaft hole 15ba, respectively, the inclination of the rotary shaft 13 rotating the forceps elevator 12 is prevented. Accordingly, even if the operation for elevating the forceps elevator 12 is repeated, it is possible to keep the watertight condition and to prevent the occurrence of an improper rotation.

When the rotary shaft is supported only on the side of the forceps elevator as in Japanese Patent Laid-Open No. 2016-131578, there is a possibility that the rotary shaft is inclined by the degree corresponding to the clearance between the rotary shaft and the housing with regard to the thickness of the portion supporting the rotary shaft. On the other hand, in the endoscope 1, there is a possibility that the rotary shaft 13 is inclined by the degree corresponding to the clearance between the rotary shaft 13 and the housing 15 with regard to the distance from the end surface of the first shaft hole 15aa on the side of the forceps elevator 12 to the end surface of the second shaft hole 15ba on the side opposite to the forceps elevator 12. Specifically, in the endoscope 1, the inclination caused due to the clearance between the rotary shaft 13 and the housing 15 is received in the distance from the end surface of the first shaft hole 15aa on the side of the forceps elevator 12 to the end surface of the second shaft hole 15ba on the side opposite to the forceps elevator 12, and therefore the rotary shaft 13 is inclined by a small degree. As a result, it is highly effective in keeping the watertight condition and preventing the occurrence of an improper rotation.

Figure 14:
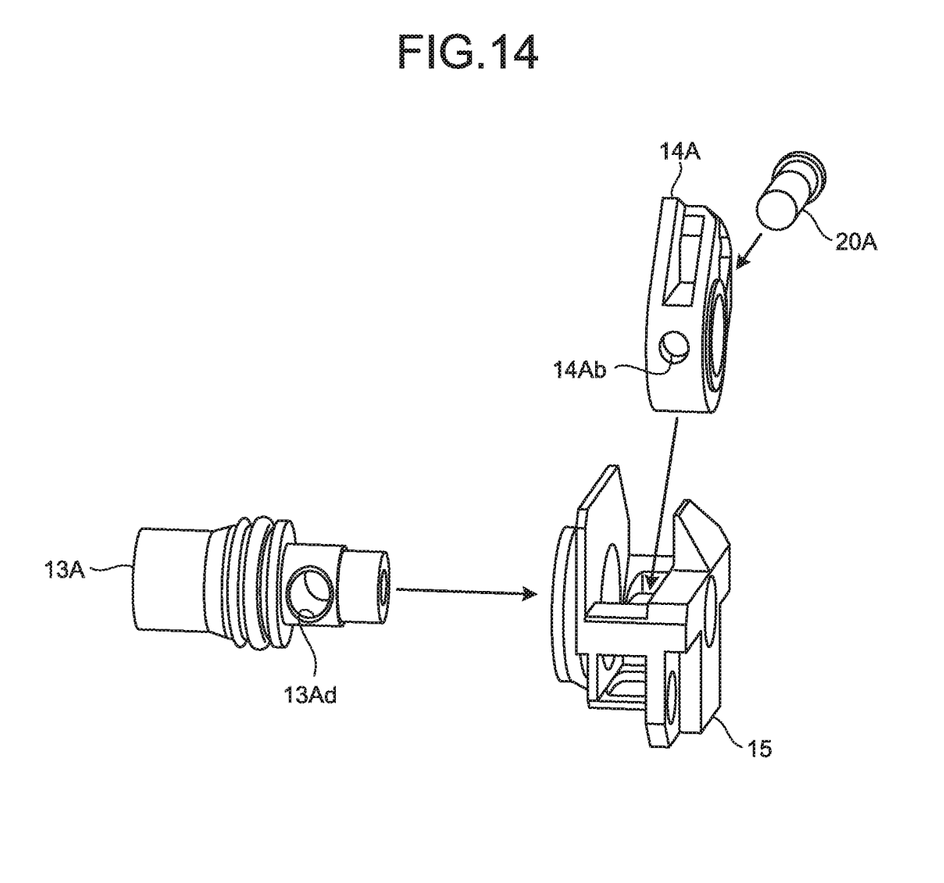
FIG. 14 is a diagram illustrating a configuration of a part of a distal end portion of an endoscope according to a modification 1 of the embodiment.

FIG. 14 is a diagram illustrating a configuration of a part of a distal end portion of an endoscope according to a modification 1 of the embodiment. As illustrated in FIG. 14, a rotary shaft 13A includes a screw hole 13Ad, and an arm unit 14A includes a screw hole 14Ab. A pin screw 20A is fitted into the screw hole 13Ad and the screw hole 14Ab. As described here, a screw may be used instead of a spring pin. The central portion of the pin screw 20A in the longitudinal direction is provided with a recessed portion to check the watertightness between the forceps elevator and the rotary shaft 13A. The formation of the recessed portion allows the gas introduced through the through-hole formed inside the rotary shaft 13A on the side opposite to the forceps elevator to move toward the forceps elevator.

Figure 15:
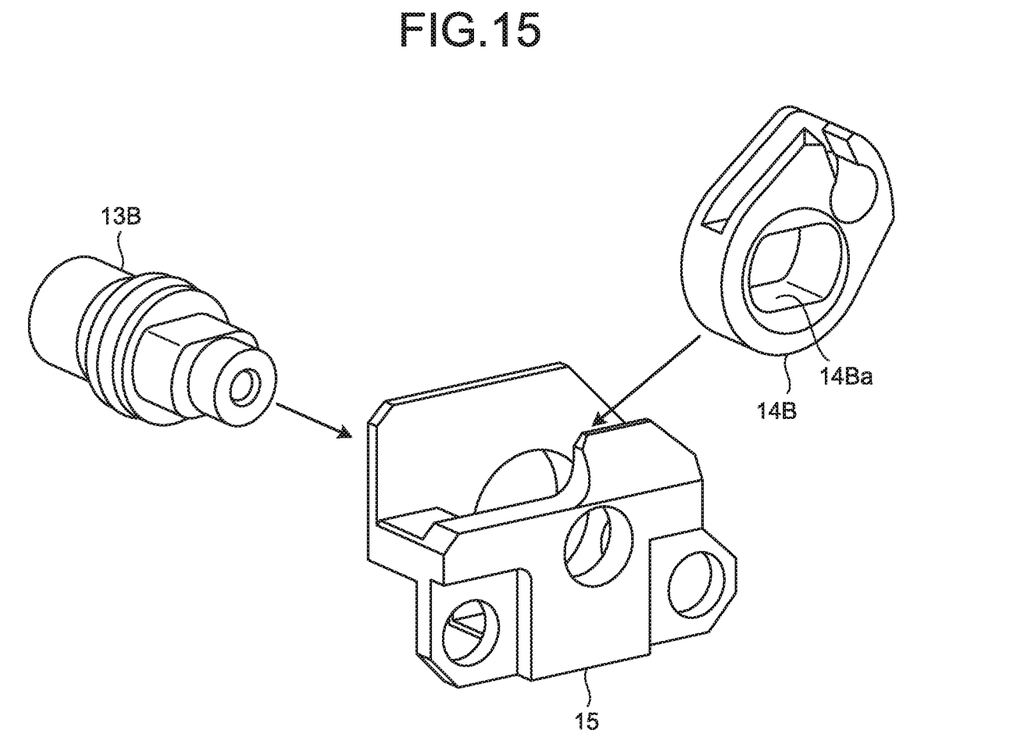
FIG. 15 is a diagram illustrating a configuration of a part of a distal end portion of an endoscope according to a modification 2 of the embodiment.

FIG. 15 is a diagram illustrating a configuration of a part of a distal end portion of an endoscope according to a modification 2 of the embodiment. As illustrated in FIG. 15, a rotary shaft 13B is pressed into a through-hole 14Ba of an arm unit 14B. As described above, the method for fixing the arm unit and the rotary shaft is not particularly limited. Also, the method for fixing the rotary shaft and the forceps elevator is not particularly limited.

In the description according to the above-described embodiment, the distal-end rigid portion 11 is made of a resin; however, the distal-end rigid portion 11 may be made of a metal or an alloy. When the distal-end rigid portion 11 is made of a metal or an alloy, the housing 15 may be directly fixed to the distal-end rigid portion 11 with a screw, or the like, without the base 21.

Other advantages and modifications may be easily derived by those skilled in the art. Therefore, broader aspects of the present disclosure are not limited to the specific details and the representative embodiments described and illustrated above. Thus, various modifications are possible without departing from the spirit or the scope of general ideas of the present disclosure as defined by the appended claims and their equivalents.

According to the present disclosure, it is possible to achieve an endoscope in which it is possible to prevent the inclination of a rotary shaft for elevating an elevator.

Additional advantages and modifications will readily occur to those skilled in the art. Therefore, the disclosure in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An endoscope through which an instrument is insertable, the endoscope comprising:
    a distal-end rigid portion disposed at a distal end of the endoscope and including an opening through which the instrument protrudes;
    a raising base disposed in the opening and configured to be in contact with the instrument and change a direction in which the instrument protrudes;
    a rotary shaft having one end thereof fixed to the raising base so as to rotate together with the raising base;
    an arm formed separately from the rotary shaft, the arm being fixed to the rotary shaft so as to rotate the rotary shaft in accordance with an operation on an operating unit, the arm and the rotary shaft having first and second mating portions, respectively, for preventing relative rotation between the arm and the rotary shaft;
    a housing formed separately from the distal-end rigid portion, the housing including:
        a first bearing located closer to the raising base than the arm in an axial direction of the rotary shaft and including a first shaft hole to rotatably support the rotary shaft; and
        a second bearing located on a side opposite to the first bearing with respect to the arm unit in the axial direction, the second bearing including a second shaft hole that is coaxially arranged with the first shaft hole so as to rotatably support the rotary shaft; and
    a seal disposed between an outer circumference of the rotary shaft and an inner circumference of the first shaft hole to keep watertightness between the rotary shaft and the first shaft hole.

2. The endoscope according to claim 1, further comprising a spring pin or a pin screw configured to fix the rotary shaft to the arm.

3. The endoscope according to claim 1, wherein
    the arm includes a through-hole, the first mating portion comprising the through-hole having a first planar portion extending in a direction perpendicular to the axial direction,
    the second mating portion comprises the rotary shaft having an outer circumference with a second planar portion extending in a direction perpendicular to the axial direction, and
    the through-hole is engaged with the rotary shaft in a state where the first planar portion of the through-hole is opposed to the second planar portion of the rotary shaft.

4. The endoscope according to claim 3, wherein the arm includes a step on one or more side surfaces of the arm surrounding a corresponding opening of the through-hole, the step protruding in the axial direction from the one or more side surfaces.

5. The endoscope according to claim 1, wherein an outer circumference of the rotary shaft includes an engagement groove with which the seal is engaged.

6. The endoscope according to claim 1, wherein a rotation axis of the raising base, a rotation axis of the arm, and axis centers of the first shaft hole and the second shaft hole are coincident with each other.

7. The endoscope according to claim 1, wherein the housing is removably attached to the distal-end rigid portion.

8. The endoscope according to claim 7, wherein the housing includes a screw hole provided along the axial direction, the screw hole being configured to fix the housing to the distal-end rigid portion.

9. The endoscope according to claim 1, further comprising an ultrasound transducer disposed at the distal end.

10. The endoscope according to claim 1, wherein a thickness of the rotary shaft where the rotary shaft contacts the second bearing is thinner than a thickness of the rotary shaft where the rotary shaft contacts the first bearing.

11. The endoscope according to claim 1, wherein the housing is a single-unitary housing having both of the first bearing and the second bearing.

12. The endoscope according to claim 1, further comprising a concave portion configured to accept a distal end of a wire for rotating the raising base, the concave portion of the arm being disposed between the first bearing and the second bearing in the axial direction.

13. An endoscope comprising:
    a distal-end rigid portion disposed at a distal end of the endoscope and including an opening through which an instrument protrudes;
    a raising base disposed in the opening and configured to be in contact with the instrument and change a direction in which the instrument protrudes;
    a rotary shaft having a first end one end thereof fixed to the raising base so as to rotate together with the raising base;
    an arm fixed to the rotary shaft so as to rotate the rotary shaft;
    a housing formed separately from the distal-end rigid portion, the housing including:
        a first bearing located closer to the raising base than the arm in an axial direction of the rotary shaft and including a first shaft hole to rotatably support the rotary shaft; and
        a second bearing located on a side opposite to the first bearing with respect to the arm unit in the axial direction, the second bearing including a second shaft hole that is coaxially arranged with the first shaft hole so as to rotatably support the rotary shaft;

a seal disposed between an outer circumference of the rotary shaft and an inner circumference of the first shaft hole to keep watertightness between the rotary shaft and the first shaft hole; and a housing seal disposed between the distal-end rigid portion and the first bearing, and configured to keep watertightness between the distal-end rigid portion and the housing.

14. The endoscope according to claim 13, wherein the arm is formed separately from the rotary shaft, the arm and the rotary shaft having first and second mating portions, respectively, for preventing relative rotation between the arm and the rotary shaft.

15. The endoscope according to claim 13, wherein the housing is a single-unitary housing having both of the first bearing and the second bearing.

16. The endoscope according to claim 13, further comprising a concave portion configured to accept a distal end of a wire for rotating the raising base, the concave portion of the arm being disposed between the first bearing and the second bearing in the axial direction.

17. An endoscope comprising:
a distal-end rigid portion including an opening through which an instrument protrudes;
a raising base disposed in the opening and configured to be in contact with the instrument and change a direction in which the instrument protrudes;
a rotary shaft having a first end fixed to the raising base so as to rotate together with the raising base;
an arm fixed to the rotary shaft;
a housing formed separately from the distal-end rigid portion, the housing including:
a first bearing located closer to the raising base than the arm in an axial direction of the rotary shaft and including a first shaft hole to rotatably support the rotary shaft; and
a second bearing located on a side opposite to the first bearing with respect to the arm in the axial direction, the second bearing including a second shaft hole that is coaxially arranged with the first shaft hole so as to rotatably support the rotary shaft; and
a seal disposed between an outer circumference of the rotary shaft and an inner circumference of the first shaft hole to keep watertightness between the rotary shaft and the first shaft hole; and
a raising base seal disposed between the rotary shaft and the raising base, the raising base seal being configured to keep watertightness between the rotary shaft and the raising base.

18. The endoscope according to claim 17, wherein the arm is formed separately from the rotary shaft, the arm and the rotary shaft having first and second mating portions, respectively, for preventing relative rotation between the arm and the rotary shaft.

19. The endoscope according to claim 17, wherein the housing is a single-unitary housing having both of the first bearing and the second bearing.

20. The endoscope according to claim 17, further comprising a concave portion configured to accept a distal end of a wire for rotating the raising base, the concave portion of the arm being disposed between the first bearing and the second bearing in the axial direction.

* * * * *